United States Patent
Cavezza et al.

(10) Patent No.: US 7,629,359 B2
(45) Date of Patent: Dec. 8, 2009

(54) USE OF PIPERIDINE DERIVATIVES AS DERMO-DECONTRACTING AGENTS

(75) Inventors: Alexandre Cavezza, Pavillon sous Bois (FR); Roger Rozot, Lagny/Marne (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/631,391

(22) PCT Filed: Jun. 15, 2005

(86) PCT No.: PCT/EP2005/007975

§ 371 (c)(1),
(2), (4) Date: Feb. 2, 2007

(87) PCT Pub. No.: WO2006/003030

PCT Pub. Date: Jan. 12, 2006

(65) Prior Publication Data

US 2007/0259915 A1    Nov. 8, 2007

Related U.S. Application Data

(60) Provisional application No. 60/589,563, filed on Jul. 21, 2004.

(30) Foreign Application Priority Data

Jul. 1, 2004    (FR)    ................... 04 51396

(51) Int. Cl.
*A61K 31/435*    (2006.01)
*A61Q 19/08*    (2006.01)
*A61K 8/49*    (2006.01)

(52) U.S. Cl. ...................... 514/317; 514/315

(58) Field of Classification Search ................. 514/317, 514/315
See application file for complete search history.

(56) References Cited

U.S. PATENT DOCUMENTS

| 4,820,717 A | 4/1989 | Mosse et al. |
| 2003/0078282 A1 | 4/2003 | Armer et al. |

FOREIGN PATENT DOCUMENTS

| EP | 1 053 745 | 11/2000 |
| EP | 1 088 548 | 4/2001 |
| EP | 405 633 | 4/2004 |
| WO | 92 02502 | 2/1992 |
| WO | 03 032969 | 4/2003 |

OTHER PUBLICATIONS

H. P. S. Chawla, et al., "Agents Acting on The Central Nervous System. XII. 3-t- Aminopropiophenones As Central Muscle Relaxants and Diuretics", Journal of Medicinal Chemistry, vol. 13, No. 3, XP 001183938, pp. 480-488, 1970.

*Primary Examiner*—Sabiha Qazi
(74) *Attorney, Agent, or Firm*—Oblon, Spivak, McClelland, Maier & Neustadt, L.L.P.

(57) ABSTRACT

The present invention relates to a cosmetic process for treating wrinkled skin, in particular the skin of the face and/or of the forehead, through a dermo-decontracting effect, comprising the topical application to said skin of a composition comprising, in a physiologically acceptable medium, at least one piperidine derivative chosen from the compounds of formula (I). These compounds make it possible to combat expression wrinkles according to a mechanism of dermo-decontraction.

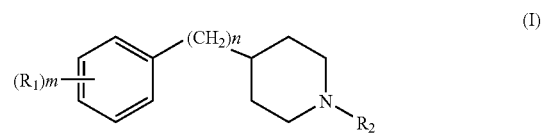

(I)

6 Claims, No Drawings

USE OF PIPERIDINE DERIVATIVES AS DERMO-DECONTRACTING AGENTS

CROSS-REFERENCE TO RELATED APPLICATIONS

The present application claims priority from International Application PCT/EP05/07975 filed Jun. 15, 2005, French Patent Application No. 04 51396 filed Jul. 1, 2004, and U.S. Provisional Patent No. 60/589,563 filed Jul. 21, 2004, the entire contents of all which are hereby incorporated by reference.

FIELD OF THE INVENTION

The present invention relates to a cosmetic process for treating wrinkled skin through a dermo-decontracting effect, comprising the topical application to said skin of a composition comprising, in a physiologically acceptable medium, at least one piperidine derivative of specific formula.

BACKGROUND OF THE INVENTION

Women, and even men, currently have a tendency to wish to look youthful for as long as possible and consequently seek to fade out the signs of age on the skin, which are reflected in particular by wrinkles and fine lines. In this respect, advertising and the fashion world talk about products intended to keep the skin radiant and wrinkle-free, which are signs of youthful skin, for as long as possible, and all the more so since the physical appearance has an effect on the psyche and/or on the morale.

Up until now, wrinkles and fine lines were treated using cosmetic products containing active agents acting on the skin, for example by improving its cell renewal or alternatively by promoting the synthesis of, or by preventing the degradation of, the elastic fibres of which skin tissue is composed.

Although these treatments make it possible to act on the wrinkles and fine lines caused by chronological or intrinsic aging, and also on those caused by photoageing, they have no effect on expression wrinkles, which require an intervention on the muscular contractile component (via muscle-relaxing agents) or dermal contractile component (via dermo-decontracting agents) of wrinkles.

Expression wrinkles are in fact the result of mechanisms that are different from those that generate wrinkles caused by aging.

Specifically, they are produced due to the effect of the strain exerted on the skin by the skin muscles that allow facial expressions. Depending on the shape of the face, the frequency of facial expressions and possible tics, they may appear as early as childhood. Age, along with certain environmental factors such as exposure to sunlight, are not involved in generating them, but may make them deeper and permanent.

Expression wrinkles are characterized by the presence of grooves around the orifices formed by the nose (nasal grooves), the mouth (perioral wrinkles and "sour-face" wrinkles) and the eyes (crow's-feet wrinkles), around which are the skin muscles, and also between the eyebrows (glabella wrinkles or lion wrinkles) and on the forehead.

Until now, the only means commonly used for acting on expression wrinkles is botulinum toxin, which is in particular injected into the wrinkles of the glabella, which are wrinkles between the eyebrows (see J. D. Carruters et al., *J. Dermatol. Surg. Oncol.*, 1992, 18, pp. 17-21).

The applicant has also proposed various compounds capable of providing a muscle-relaxing effect when they are applied topically to the skin, thus making it possible to act on expression wrinkles via another route. Among these compounds, mention may in particular be made of calcium channel-associated receptor antagonists, such as verapamil (FR-2 793 681), and in particular manganese and its salts (FR-2 809 005), and alverine (FR-2 798 590); chloride channel-associated receptor agonists, including glycine (EP-0 704 210) and certain extracts of *Iris pallida* (FR-2 746 641); and sapogenins (EP-1 352 643).

Along with these muscle-relaxing agents, the applicant has described various dermo-decontracting compounds, and in particular amine compounds (EP-1 405 633).

However, there is still a need for compounds that are more effective than those of the prior art for smoothing or fading out expression wrinkles.

SUMMARY OF THE INVENTION

Now, the applicant has discovered, surprisingly, that certain piperidine derivatives can satisfy this need. Specifically, it has been demonstrated that these compounds make it possible to relax or decontract the dermal contractile cells that are supposed to be involved in generating expression wrinkles. It is in fact thought that the phenotype of certain fibroblasts located along the tension lines created due to skin muscle contractions during facial expressions is gradually modified under the effect of these contractions, thus conferring specific contractile properties on these fibroblasts. The decontraction of these cells will thus make it possible to act on another component of expression wrinkles.

DETAILED DESCRIPTION OF THE INVENTION

Among the compounds used according to the invention, several have already been described as calcium channel inhibitors in applications EP-0 542 846 and JP-61 027 963 and in U.S. Pat. No. 4,952,560.

However, the applicant had demonstrated that, while calcium channel inhibitors are, a priori, muscle relaxing agents according to the teaching of application FR-2 793 681, they are not all dermo-decontracting agents. In particular, cinnarizine, diltiazem, nitrendipine and diazepam, which are known anti-calcium compounds (either because they act directly on calcium channels or because they act on chloride channels and thus generate an anti-calcium effect) and the muscle relaxing effect of which has—at least as regards diazepam—been demonstrated, are not active as dermo-decontracting agents in the test presented in Example 1 hereinafter. It was not therefore possible to predict that the compounds used according to the present invention, also known as calcium channel inhibitors, would have a dermo-decontracting effect.

In addition, dermo-decontraction is a phenomenon that results from the phosphorylation of the myosin light chain. This phosphorylation is modulated by many factors, for instance the activity of the myosin light chain-specific phosphatase. Now, calcium channel inhibitors do not affect this pathway. There is therefore nothing that implies that some of these inhibitors may have a dermo-decontracting effect.

Among the compounds used according to the present invention, ifenprodil has already been described as an anti-glycation agent for the treatment of age-, diabetes- and smoking-related complications (WO 03/032969), for promoting blood circulation and moisturizing the skin (JP-62 226 909 and U.S. Pat. No. 4,952,560) and in hair products (JP-62 270

514). Other piperidine derivatives have been described as antibacterial agents (EP-0 308 328).

On the other hand, to the applicant's knowledge, the use of these piperidine derivatives for combating wrinkles, in particular expression wrinkles, and/or for decontracting the skin and/or relaxing the features, has never been suggested.

A subject of the present invention is therefore a cosmetic process for treating wrinkled skin, in particular the skin of the face and/or of the forehead, through a dermo-decontracting effect, comprising the topical application to said skin of a composition comprising, in a physiologically acceptable medium, at least one piperidine derivative chosen from the compounds of formula (I):

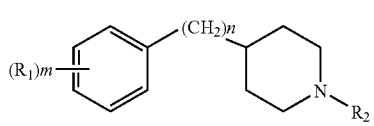

in which:

$R_1$ denotes a halogen or a radical chosen from: a $C_1$-$C_6$ alkyl radical, an OR group, an NRR' group, a $CF_3$ group, an NHCOR group or a CONRR' group;

$R_2$ denotes a linear or branched $C_1$-$C_{20}$ alkyl or alkenyl radical optionally substituted with at least one OR, COOR, =O, NRR', NHCOR or CONRR' group or with a phenyl group optionally substituted with one or more radicals $R_1$;

where R and R' denote, independently of one another, a hydrogen atom or a $C_1$-$C_6$ alkyl radical, m ranges from 0 to 5;

n ranges from 0 to 5;

and their salts and optical isomers.

A subject of the invention is also the cosmetic use of at least one piperidine derivative as defined above, as a dermo-decontracting agent for combating wrinkles, in particular expression wrinkles, and/or for decontracting the skin and/or relaxing the features.

In formula (I), the alkyl groups may in particular be chosen, according to the case, from the groups: methyl, ethyl, n-propyl, isopropyl, n-butyl, isobutyl, tert-butyl, pentyl, hexyl, heptyl, octyl, nonyl, decyl, undecyl, dodecyl, myristyl, palmityl, stearyl and arachidyl.

In addition, in the context of this application, the term "alkenyl" is intended to mean radicals possibly comprising one or more double bonds, that may or may not be conjugated. They may in particular be chosen, according to the case, from the groups: vinyl, allyl, butenyl or pentenyl.

As salts of the compound of formula (I), mention may be made of the salts obtained by addition of the compound of formula (I) with an inorganic acid, chosen in particular from hydrochloric acid, sulphuric acid and phosphoric acid, or with an organic acid, chosen in particular from acetic acid, propionic acid, succinic acid, fumaric acid, maleic acid, lactic acid, glycolic acid, citric acid and tartaric acid.

Preferably, the piperidine derivative according to the invention is such that at least one, and preferably all, of the following conditions are satisfied:

m ranges from 0 to 3, and is preferably equal to 0, n is equal to 0 or 1, $R_1$ denotes a methoxy radical or trifluoromethyl radical, $R_2$ denotes a linear or branched $C_1$-$C_6$ alkyl or alkenyl radical optionally substituted with a phenyl group.

It is advantageously 4-phenyl-1-(4-phenylbutyl)piperidine or one of its salts, such as its maleic acid salt (commercially available), or else 4-benzyl-1-hexylpiperidine or one of its salts.

The compounds of formula (I) can in particular be prepared according to the following reaction scheme:

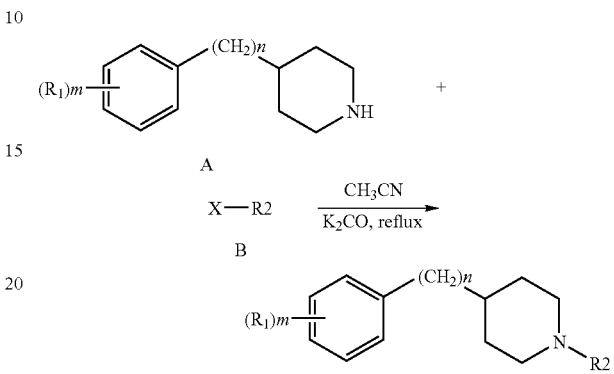

by reacting one equivalent of substituted piperidine A with one equivalent of B, where X denotes a leaving group of halogen or sulphonate type, in the presence of $K_2CO_3$ in acetonitrile at reflux overnight. The product obtained can be treated and purified on a silica column.

The amount of piperidine derivative that can be used according to the invention depends of course on the desired effect and can therefore vary to a large extent.

To give an order of magnitude, these derivatives can be used in an amount representing from 0.01% to 10% of the total weight of the composition, preferably in an amount representing from 0.05% to 5% of the total weight of the composition, more preferably in an amount representing from 0.1% to 2% of the total weight of the composition.

The composition used according to the invention is suitable for topical application to the skin, and it therefore contains a physiologically acceptable medium, i.e. a medium that is compatible with the skin and optionally with its integuments (eyelashes, nails, hair) and/or the mucous membranes. This medium is advantageously cosmetically acceptable, i.e. it does not result in itching, stinging or redness that may put off the user of the composition, and it has a pleasant appearance, smell and feel.

This composition may be provided in any of the pharmaceutical forms normally used in the cosmetics field, and in may in particular be in the form of an optionally gelled solution, of a dispersion of the lotion type, optionally a two-phase lotion, of an emulsion obtained by dispersion of a fatty phase in an aqueous phase (O/W) or vice versa (W/O), or of a triple emulsion (W/O/W or O/W/O) or of a vesicular dispersion of ionic and/or non-ionic type. These compositions are prepared according to the usual methods. According to this invention, it is preferable to use a composition in the form of an oil-in-water emulsion.

This composition may be more or less fluid and may have the appearance of a white or coloured cream, of an ointment, of a milk, of a lotion, of a serum, of a paste or of a mousse. It may optionally be applied in the form of an aerosol. It may also be provided in solid form, in particular in the form of a stick. It may be used as a care product and/or as a makeup product for the skin.

In a known manner, the composition used according to the invention may also contain the adjuvants that are usual in the cosmetics field, such as hydrophilic or lipophilic gelling agents, hydrophilic or lipophilic active agents, preserving agents, antioxidants, solvents, fragrances, fillers, screening agents, pigments, odour absorbers and dyes. The amounts of these various adjuvants are those conventionally used in the field under consideration, and for example from 0.01 to 20% of the total weight of the composition. Depending on their nature, these adjuvants may be introduced into the fatty phase, into the aqueous phase or into the lipid vesicles. In any event, these adjuvants, and the proportions thereof, will be chosen so as not to harm the desired properties of the piperidine derivatives according to the invention.

When the composition used according to the invention is an emulsion, the proportion of the fatty phase may range from 5 to 80% by weight, and preferably from 5 to 50% by weight, relative to the total weight of the composition. The oils, the emulsifiers and the co-emulsifiers used in the composition in the form of an emulsion are chosen from those conventionally used in the field under consideration. The emulsifier and the co-emulsifier are present in the composition in a proportion ranging from 0.3 to 30% by weight, and preferably from 0.5 to 20% by weight, relative to the total weight of the composition.

As oils that may be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids or waxes (carnauba wax, ozokerite) may also be used as fats.

As emulsifiers and co-emulsifiers that may be used in the invention, mention may, for example, be made of fatty acid esters of polyethylene glycol, such as PEG-100 stearate, and fatty acid esters of glycerol such as glyceryl stearate.

As hydrophilic gelling agents/thickeners, mention may in particular be made of carboxyl vinyl polymers (carbomer), acrylic copolymers such as acrylate/alkyl acrylate copolymers, polyacrylamides, polysaccharides, natural gums and clays, and as lipophilic gelling agents/thickeners, mention may be made of modified clays such as bentones, metal salts of fatty acids, and hydrophobic silica.

As active agents, it will be advantageous to introduce into the composition used according to the invention at least one compound chosen from: desquamating agents; moisturizers; depigmenting or propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; the other muscle-relaxing agents and/or other dermo-decontracting agents; tensioning agents; anti-pollution agents and/or free-radical scavengers; agents that act on the microcirculation; agents that act on the energy metabolism of cells; and mixtures thereof.

Examples of such additional compounds are: retinol and its derivatives such as retinyl palmitate; ascorbic acid and its derivatives such as magnesium ascorbyl phosphate and ascorbyl glucoside; tocopherol and its derivatives such as tocopheryl acetate; nicotinic acid and its precursors such as nicotinamide; ubiquinone; glutathione and its precursors such as L-2-oxothiazolidine-4-carboxylic acid; plant extracts and in particular plant proteins and hydrolysates thereof, and also phytohormones; marine extracts such as algal extracts; bacterial extracts; sapogenins, such as diosgenin, and extracts of Wild Yam containing them; ceramides; hydroxy acids; hydroxy acids such as salicylic acid and 5-n-octanoylsalicylic acid; resveratrol; oligopeptides and pseudopeptides and acylated derivatives thereof; manganese salts and magnesium salts, in particular gluconates; and mixtures thereof.

As indicated above, the composition according to the invention may also contain photoprotective agents that are active in the UVA and/or the UVB range, in the form of organic or inorganic compounds, the latter being optionally coated in order to make them hydrophobic.

The organic photoprotective agents can in particular be chosen from: anthranilates, in particular menthyl anthranilate; benzophenones, in particular benzophenone-1, benzophenone-3, benzophenone-5, benzophenone-6, benzophenone-8, benzophenone-9, benzophenone-12, and preferably benzophenone-3 (oxybenzone), or benzophenone-4 (Uvinul MS40 available from BASF); benzylidenecamphors, in particular 3-benzylidenecamphor, benzylidenecamphorsulphonic acid, camphor benzalkoniummethosulphate, polyacrylamidomethylbenzylidenecamphor, terephthalylidinedicamphorsulphonic acid, and preferably 4-methylbenzylidenecamphor (Eusolex 6300 available from Merck); benzimidazoles, in particular benzimidazilate (Neo Heliopan AP available from Haarmann and Reimer), or phenylbenzimidazolesulphonic acid (Eusolex 232 available from Merck); benzotriazoles, in particular drometrizole trisiloxane, or methylenebisbenzotriazolyltetramethylbutylphenol (Tinosorb M available from Ciba); cinnamates, in particular cinoxate, DEA methoxycinnamate, diisopropyl methylcinnamate, glyceryl ethylhexanoate dimethoxycinnamate, isopropyl methoxycinnamate, isoamyl cinnamate and, preferably, ethocrylene (Uvinul N35 available from BASF), octyl methoxycinnamate (Parsol MCX available from Hoffmann La Roche), or octocrylene (Uvinul 539 available from BASF); dibenzoylmethanes, in particular butylmethoxydibenzoylmethane (Parsol 1789); imidazolines, in particular ethylhexyl dimethoxybenzylidene dioxoimidazoline; PABAs, in particular ethyl dihydroxypropyl PABA, ethylhexyldimethyl PABA, glyceryl PABA, PABA, PEG-25 PABA and, preferably, diethylhexylbutamidotriazone (Uvasorb HEB available from 3V Sigma), ethylhexyltriazone (Uvinul T150 available from BASF) or ethyl PABA (benzocaine); salicylates, in particular dipropylene glycol salicylate, ethylhexyl salicylate, homosalate or TEA salicylate; triazines, in particular anisotriazine (Tinosorb S available from Ciba).

The inorganic photoprotective agents preferably consist of zinc oxide and/or titanium dioxide, preferably of nanometric size, optionally coated with alumina and/or stearic acid.

The composition according to the invention is advantageously intended to be applied to areas of the face and/or of the forehead that are marked with expression wrinkles, and/or on individuals with expression wrinkles.

The wrinkles concerned are preferably those lying radially around the mouth and/or the eyes, in particular the crow's-feet wrinkles, and/or lying on the forehead, in particular the "lion" wrinkle, located in the glabella, in between the eyebrows, and/or lying horizontally on the forehead.

The invention will now be illustrated by means of the following non-limiting examples. In these examples, the amounts are indicated as percentages by weight.

EXAMPLES

Example 1

Demonstration of the Dermo-Decontracting Effect of the Piperidine Derivatives According to the Invention a) Principle of the Test The principle of this test consists in studying the decontracting effect of the maleic acid salt of 4-phenyl-1-(4-phenylbutyl)piperidine (commercially available from one of the companies Biomol, ICN, Nacalai and Tocris), on a dermis equivalent model consisting of a matrix of collagen seeded with normal human fibroblasts.

These conditions are intended to mimic, in vitro, the dermal contractile phenomena that occur during facial expressions. Under these conditions, in fact, the cells spontaneously express tensile forces that induce a retraction of the collagen gel. As a result of this, there is a decrease in the total surface area of the dermis equivalent over time. Measurement of this surface area makes it possible to evaluate the relaxing effects of the substances brought into contact with the dermis equivalent beforehand.

b) Protocol

Two series of attached dermis equivalents containing normal human fibroblasts are prepared: a control series without any treatment, and a series treated with the test compound (1 µM). The experiment is repeated three times.

The dermis equivalents are prepared as described in Asselineau et al., *Exp. Cell. Res.*, 1985, 159, 536-539; Models in dermatology, 1987, Vol. 3 pp. 1-7, in the following proportions:

| MEM medium (1.76X) with or without compound | 45% |
|---|---|
| Foetal calf serum: | 10% |
| NaOH (0.1N): | 5% |
| Acetic acid (1/1000): | 4% |
| Collagen: | 26% |
| Fibroblasts: | 11% |

The treated dermis equivalent differs from the control dermis equivalents in that 1 µM of the test compound is added thereto.

The collagen used is type I collagen (commercial solution). It is extracted from rat tails or from calf skin by acid hydrolysis and is conserved in an acidic medium at +4° C.; it polymerizes naturally by reheating to 37° C. and by a decrease in the degree of acidity. The collagen is dialysed beforehand against successive baths of water+acetic acid.

The protocol is as follows: the 1.76×MEM medium in the presence of additives (1% glutamine, 1% nonessential amino acids, 1% sodium pyruvate, 1% fungizone and 1% Penicillin/Streptomycin), the foetal calf serum and the 0.1 N sodium hydroxide NaOH are introduced into a 50 ml centrifuge tube kept in crushed ice. The fibroblasts isolated form human skin explants are then added at a concentration of $1.5 \times 10^5$ cells per 1 ml of culture medium.

A volume/volume mixture of collagen in acetic acid at 1/1000 is then added slowly, along the wall of the tube so as to observe the appearance of a whitish cloud.

The entire combination is then carefully mixed and dispensed into the wells of a 12-well culture plate (Costar type, reference 3512) in a proportion of 2 ml of mixture per well. The final cell concentration is $3 \times 10^4$ cells/dermis equivalent, with a final collagen concentration of 1 mg/ml. The culture plate is then placed in an incubator at 37° C. with 5% $CO_2$.

Once formed after polymerization of the collagen, the dermis equivalents are left adherent to the culture support for 3 days and are then detached from the support so that the contraction may begin. These attached dermis equivalents are taken out of the incubator in order to take the pictures for the purpose of measuring their surface area, for each point of the contraction kinetics (0, 4, 8 and 24 hours). They are immediately returned to the incubator between each measurement point.

The spontaneous contraction of the dermis equivalent that is treated (with the test compound) and the control dermis equivalent (without test compound) is evaluated by measuring their surface area, at various times after the beginning of the spontaneous contraction.

For this, a digital image is acquired for each treated or nontreated dermis equivalent, by means of a camera (CCD camera—Iris Sony DXC-107P) and the surface area is then calculated on each image by means of an image analysing system (Zeiss Axiovision 3.0). Correspondent to this surface area measurement is a percentage contraction equal to the ratio of the surface areas according to the formula:

$$\% \text{ contraction} = (Sp-Si)/Sp \times 100$$

where:

'Sp' represents the surface area of a well of the culture plate; it corresponds to the total surface area of the dermis equivalent before contraction, 'Si' represents the surface area of the dermis equivalent at the moment i of the contraction kinetics.

c) Results

The maleic acid salt of 4-phenyl-1-(4-phenylbutyl)piperidine reduces the contraction of the fibroblasts by 17%, on average, over the duration of the experiment, compared with the control. This compound therefore has a significant dermo-decontracting effect.

Example 2

Synthesis of 4-phenyl-1-(4-phenylbutyl)piperidine

This compound was prepared according to the following reaction scheme:

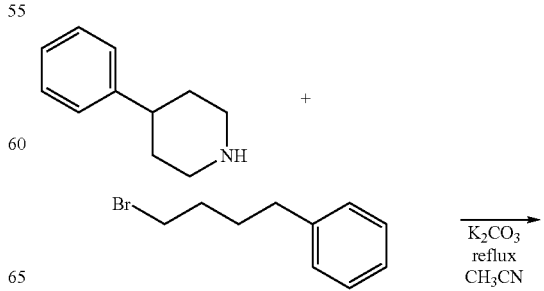

-continued

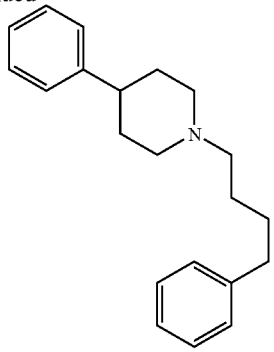

4-Phenylpiperidine (1 eq) was reacted with 4-phenylbromobutyl (1 eq) in the presence of $K_2CO_3$ in acetonitrile at reflux overnight. The product obtained was treated and purified on a silica column. The $^1$H NMR at 500 MHz is in accordance with the expected structure.

Example 3

Cosmetic Composition

This composition is prepared in a manner that is conventional for those skilled in the art. The amounts given in this example are indicated as percentages by weight.

| | |
|---|---|
| 4-Phenyl-1-(4-phenylbutyl)piperidine | 0.10% |
| Stearic acid | 3.00% |
| Mixture of glyceryl monostearate and polyethylene glycol stearate (100 EO) | 2.50% |
| Polyethylene glycol stearate (20 EO) | 1.00% |
| Cyclopentadimethylsiloxane | 10.00% |
| Fillers | 3.00% |
| Plant oils | 7.00% |
| Synthetic oils | 6.00% |
| Preserving agents | 1.20% |
| Oxyethylenated (16 EO) dimethylsiloxane with methoxy ends | 1.00% |

-continued

| | |
|---|---|
| Silicone gum | 0.20% |
| Acrylic copolymer in an inverse emulsion (Simulgel 600 from Seppic) | 1.70% |
| Stearyl alcohol | 1.00% |
| Water | qs 100% |

This cream is intended to be applied to the face and the forehead in order to relax the features and decontract the facial skin.

The invention claimed is:

1. A process for treating wrinkled skin, comprising topically applying a composition to the skin, the composition comprising 4-phenyl-1-(4-phenylbutyl)piperidine or a salt thereof.

2. Process according to claim 1, wherein:
the composition comprises a salt of 4-phenyl-1-(4-phenylbutyl)piperidine; and
the salt is obtained by reacting 4-phenyl-1-(4-phenylbutyl)piperidine with an inorganic acid selected from the group consisting of hydrochloric acid, sulphuric acid and phosphoric acid.

3. Process according to claim 1, wherein:
the composition comprises a salt of 4-phenyl-1-(4-phenylbutyl)piperidine; and
the salt is obtained by reacting 4-phenyl-1-(4-phenylbutyl)piperidine with an organic acid selected from the group consisting of acetic acid, propionic acid, succinic acid, fumaric acid, maleic acid, lactic acid, glycolic acid, citric acid and tartaric acid.

4. Process according to claim 1, wherein the composition comprises a maleic acid salt of 4-phenyl-1-(4-phenylbutyl)piperidine.

5. Process according to claim 1, wherein applying the composition to the skin comprises applying the composition to expression wrinkles.

6. The process according to claim 1, wherein topically applying the composition to the skin comprises topically applying a dermo-decontracting effective amount of the composition to the skin.

* * * * *